United States Patent [19]

Ricci

[11] Patent Number: 5,073,719

[45] Date of Patent: Dec. 17, 1991

[54] APPARATUS FOR THE EVALUATION OF THE ERYTHROSEDIMENTATION RATE AND OTHER

[75] Inventor: Antonio Ricci, Monteriggioni, Italy

[73] Assignee: Diesse Diagnostica Senese S.r.l., Milan, Italy

[21] Appl. No.: 583,800

[22] Filed: Sep. 14, 1990

[30] Foreign Application Priority Data

Sep. 26, 1989 [IT] Italy ............................ 11708/89[U]

[51] Int. Cl.$^5$ ............................................ G01N 15/06
[52] U.S. Cl. ..................................... 250/573; 356/39
[58] Field of Search ................. 250/573, 576; 356/39, 356/442, 219, 220; 128/637, 632, 691

[56] References Cited

U.S. PATENT DOCUMENTS 3,781,118 12/1973 Graham .............................. 356/442
4,774,056 9/1988 Ricci et al. ............................ 356/39
4,848,900 7/1989 Kuo et al. .............................. 356/39

Primary Examiner—David C. Nelms
Assistant Examiner—Que T. Le
Attorney, Agent, or Firm—McGlew & Tuttle

[57] ABSTRACT

An apparatus for measuring the erythrosedimentation rate and carrying out other similar analyses through photometric reading, comprises one or more seats (9, 11) for receiving test tubes (P) inclined to a limited extent with respect to the vertical. Guide means (13) are provided for a skid (15) which is able to slide parallel to the test tube(s) (P) introduced into said seat(s) for the reading. On said skid (15), there are provided emitting and receiving members (19A, 19B) for a signal of optical type which goes through the or each test tube (P) during the reading scan. A motorization (3,5) moves said skid (15) along the test tube(s) for performing reading of the latter.

5 Claims, 2 Drawing Sheets

APPARATUS FOR THE EVALUATION OF THE ERYTHROSEDIMENTATION RATE AND OTHER

The object of the invention is to provide an apparatus for measuring the erythrosedimentation rate and carrying out other similar analyses through photometric reading, which apparatus is simplified and reduced in dimensions with respect to currently known devices, and of high performance especially for the number of analyses which it is able to perform.

In practice, the present apparatus comprises: one or more seats for receiving test tubes inclined to a limited extent with respect to the vertical; guide means for a skid able to slide parallel to the test tube(s) introduced into said seat(s) for the reading; on said skid, members for the emission and reception of an optical signal which goes through the or each test tube during the reading scan; and a motorization for the displacements of said skid.

The motorization may comprise a threaded shaft driven by a motor, said shaft engaging a threaded bush carried by said skid.

The apparatus may further comprise means for evaluating the skid position when a signal is received by said signal-receiving means relevant to the or each test tube. Said means for evaluating the skid position may take the form of means for measuring the angular position of the threaded shaft. Means may also be provided to limit the skid travel and to reset the reading means.

The drawing shows a possible embodiment of the invention, and in particular:

Figure 1:
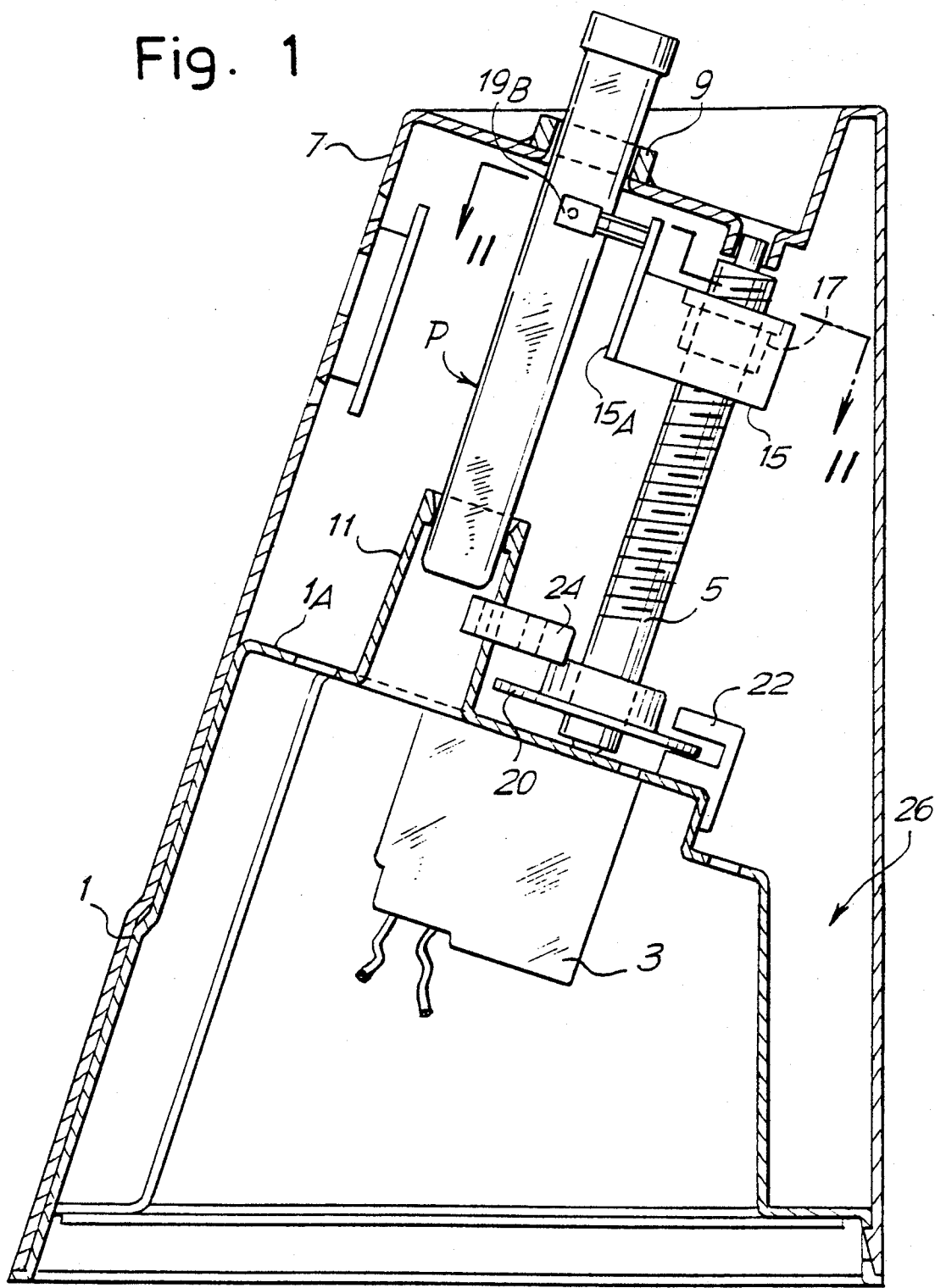
FIG. 1 is a vertical schematic section.
Figure 2:
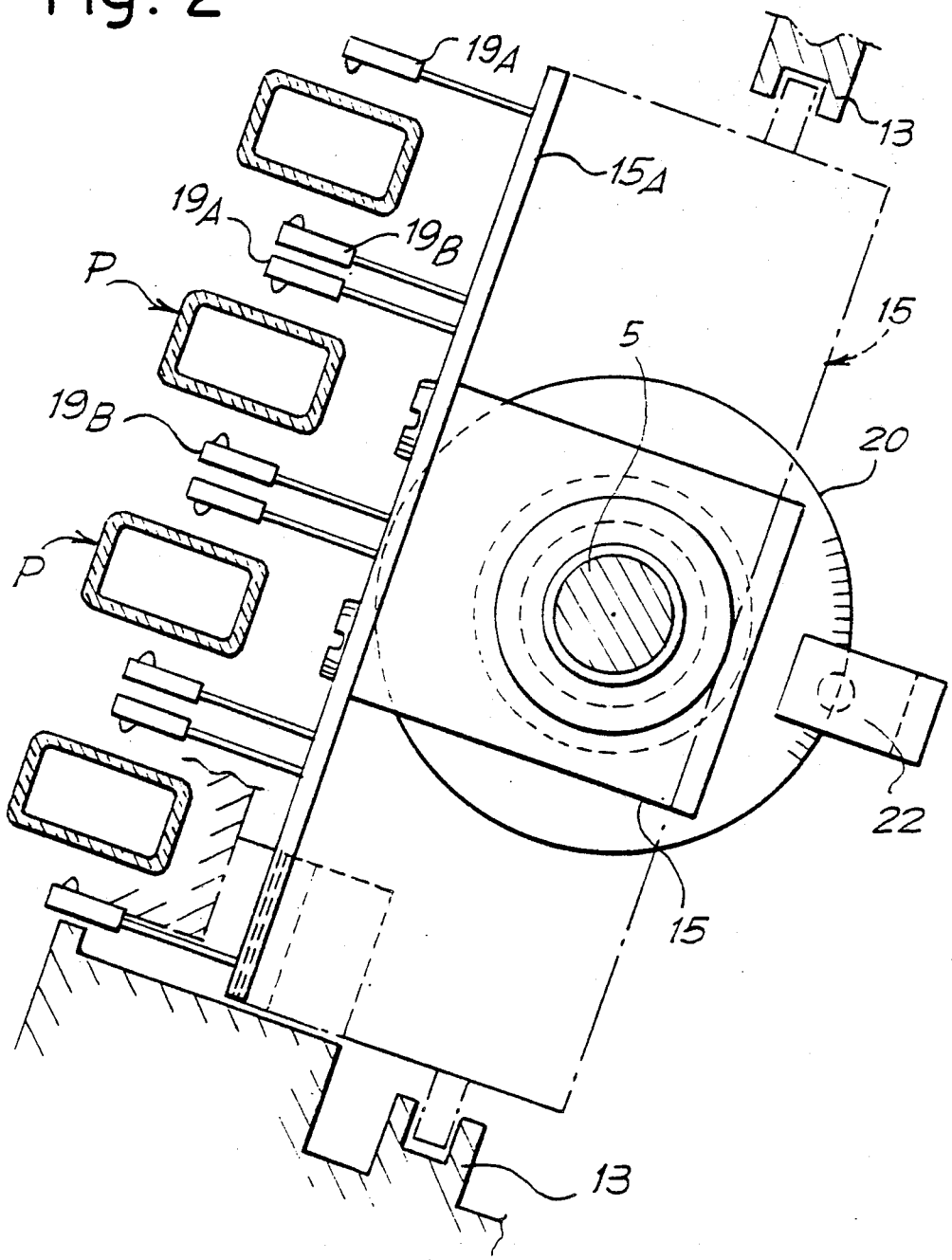
FIG. 2 is a local section taken on line II—II in FIG. 1.

According to what is illustrated in the attached drawing, 1 indicates a base structure having an upper wall 1A slighlty inclined to the horizontal, and below which a motor-reducer 3 is attached which is able to drive a threaded shaft 5 developing perpendicularly from the wall 1A. Extending above the wall 1 is a cover section 7 which makes up a through seat 9 lined up with a seat 11 stemming from the wall 1A to receive a test tube P which holds the liquid to be analyzed. The apparatus may comprise a single seat 9 and 11 for a single test tube P or multiple seats lined up for a plurality of test tubes as indicated in FIG. 2. The test tube(s) is(are) parallel to the shaft 5. The shape used for the test tubes P is advantageously of rectangular cross-section and has an elongated development on a vertical plane passing through the axis of shaft 5. Parallel to the shaft 5, on the sides of the cover section 7 of the apparatus 1, guides 13 are provided which allow a skid 15 to slide parallel to the axis of shaft 5 without rotations, said skid being thus able to slide parallel to the inclined axis of the shaft 5 and to be driven by the rotation of the threaded shaft 5 by engagement of the same skid with a threaded bush 17 which is engaged with the skid 15 and the threading of shaft 5. Accordingly, by driving the shaft 5 in the two directions it is possible to cause sliding displacements of the skid 17 both upwards and downwards. The skid 15 carries a crossbar 15A which, in case of multiple lined up test tubes P, develops throughout the front thereof. The plate 15A carries pairs of optical emitting and receiving members 19A, 19B which are placed on the sides of the or each test tube P, so that a beam of light-type energy emitted by the emitting member and received by the receiving member goes through the relevant test tube in correspondence of the planar walls where it has the most limited width. By the sliding of skid 15 it is thus possible to read the transparency degree of the liquid along the test tube and, in particular, to detect the region at which an opacization of the liquid begins due to the sedimentation. Due to weel known phenomena, the sedimentation is made easier by the limited inclination of the axis of the test tubes, corresponding to the inclination of the axis of shaft 5, thereby achieving an acceleration of the process. Assessment of the position of the skid 15 at any instant is made possible through a suitable system for reading the rotations of shaft 5 which determine the skid positions along the displacement direction parallel to the axis of the same shaft 5. To this end, the shaft 5 may be provided with an indexed disc 20 having graduations able to be read by an optical reader 22 of a type known per se. With the provision of a computerization system it is possible to evaluate, through the rotation of shaft 5 and thus of disc 20, the instantaneous position of skid 15, 15A and, accordingly, of the emitting and receiving members 19A, 19B. To the graduated disc 20 a system may also be associated to define travel limit positions of the skid, by providing, for example, a further reader unit generically indicated by 24. When the apparatus has multiple seats, and test tubes P are inserted into more seats after stirring, as typically provided in certain tests as in the test for determining the erythrosedimentation rate, it is possible to achieve a fairly easy, although not entirily automated, evaluation of erythrosedimentation rate or similar evaluations through successive readings of the sedimentation level, as obtained with successive strokes of the skid 15 which are carried out at predetermined time intervals.

The apparatus is particularly suitable in cases in which a relative limited number of tests are required. It is even possible to provide a more compact embodiment than the one herein illustrated, which allows the same apparatus to be carried along by the medical or paramedical operator up to the patient's house. In this case it is possible to provide for the installation of an energy source consisting of possibly rechargeable electrical accumulators, which may be received in housings disposed, for example, in a zone 26 of the apparatus case or, anyway, in such zones as to allow a maximum reduction of the overall dimensions of the apparatus.

I claim:

1. An apparatus for measuring the erythrosedimentation rate and carrying out other similar analyses through photometric reading, comprising: one or more seats (9, 11) for receiving test tubes (P) inclined to a limited extent with respect to the vertical; guide means (13) for a skid (15) able to slide parallel to the test tube(s) (P) introduced into said seat(s) for the reading; on said skid (15), emitting and receiving members (19A, 19B) for a signal of optical type which goes through the or each test tube (P) during the reading scan; and a motorization (3, 5) for the displacements of said skid (15).

2. Apparatus according to claim 1, wherein said motorization (3, 5) comprises a threaded shaft (5) driven by a motor-reducer (3), said shaft engaging a threaded bush (17) carried by said skid (15, 15A).

3. Apparatus according to claim 1 comprising means (20, 22) for evaluating the position of the skid (15) when a signal is received from said signal-receiving means relevant to the or each test tube.

4. Apparatus according to claim 3, wherein said means for evaluating the skid position are developed as means capable of determining the angular position of the threaded shaft (5).

5. Apparatus according to claim 1, comprising means (24) for limiting the skid stroke and for resetting the reading means.

* * * * *